United States Patent [19]

Murayama et al.

[11] Patent Number: 5,672,656
[45] Date of Patent: Sep. 30, 1997

[54] TEMPERATURE SENSITIVE WATER ABSORBING AND DISCHARGING POLYMER COMPOSITION

[75] Inventors: Teiichi Murayama; Takashi Maruyama, both of Yatsushiro, Japan

[73] Assignee: Kohjin Co., Ltd., Tokyo, Japan

[21] Appl. No.: 513,883

[22] PCT Filed: Feb. 10, 1995

[86] PCT No.: PCT/JP95/00183

§ 371 Date: Sep. 5, 1995

§ 102(e) Date: Sep. 5, 1995

[87] PCT Pub. No.: WO95/21876

PCT Pub. Date: Aug. 17, 1995

[30] Foreign Application Priority Data

| Feb. 10, 1994 | [JP] | Japan | 6-036387 |
| Sep. 28, 1994 | [JP] | Japan | 6-257349 |

[51] Int. Cl.$^6$ .................... C08L 33/26; C08L 33/02
[52] U.S. Cl. .................................. 524/831; 524/832
[58] Field of Search ............ 526/304; 524/831, 524/832

[56] References Cited

U.S. PATENT DOCUMENTS

| 3,927,199 | 12/1975 | Micchelli et al. | 424/47 |
| 4,071,650 | 1/1978 | Gross | 526/304 |
| 5,447,970 | 9/1995 | Tomita et al. | 523/201 |

FOREIGN PATENT DOCUMENTS

| 61-55180 | 3/1986 | Japan . |
| 61-58657 | 3/1986 | Japan . |
| 61-247716 | 11/1986 | Japan . |
| 2-215863 | 8/1990 | Japan . |
| 4139206 | 5/1992 | Japan . |
| 4-139206 | 5/1992 | Japan . |
| 4-298203 | 10/1992 | Japan . |

OTHER PUBLICATIONS

"Vol.–Phase Transitions of Ionized N–Isopropylacrylamide Gels", by Hirotsu et al., *J. Chem Phys.*, vol. 87, No. 2, 15 Jul., 1987, pp. 1392–1395.

"Effect of Salt Solution On Selling or Shrinking Behavior of Poly(Vinylmethylether) Gel (PVMEG)" by Huang et al., *J. Chem Eng. of Japan*, vol. 21, No. 1, 3 Apr., 1988, pp. 11–14.

"Synthesis and Characterization of Thermally Reversible Macroporous Poly(N–Isopropylacrylamide) Hydrogels", by Wu et al., *J. POLYM. SOC.*, Part A: Polymer Chemistry vol. 30, 1992, pp. 2121–2129.

"Synthesis of Fast Response, Temperature–Sensitive Poly(N–Isopropylacrylamide) Gel", by Kabra et al., *POLYMER COMMUNICATIONS*, vol. 32, No. 11, 1991, pp. 322–323.

*Primary Examiner*—Joseph L. Schofer
*Assistant Examiner*—Wu C. Cheng
*Attorney, Agent, or Firm*—Oliff & Berridge

[57] ABSTRACT

A temperature sensitive water absorbing and discharging polymer composition having a predetermined selected temperature sensing point, which controls water absorbability, is obtained by polymerizing in an aqueous solution N-alkyl acrylamide derivatives with acrylic acid, alkali metal salts of acrylic acid or mixtures thereof, and diacetone acrylamide. The temperature sensitive water absorbing and water discharging polymer composition is modified to control the temperature sensing point and has a high water discharging and absorbing property above and below the temperature sensing point. The composition is utilized in a wide variety of sanitary materials such as paper diapers, soil improvers in agricultural and horticultural fields for plants and vegetables such as soil water supplying agents or soil water retaining agents, water proof sealing materials, sandbags, temperature sensors, chemical valves, solid-liquid separation materials and liquid concentrating materials.

20 Claims, No Drawings

TEMPERATURE SENSITIVE WATER ABSORBING AND DISCHARGING POLYMER COMPOSITION

FIELD OF THE INVENTION

The present invention concerns a novel water absorbing resin having water absorbability that changes significantly at temperatures near room temperature and provides water absorption and discharge depending on ambient temperature.

BACKGROUND

Water absorbing resins have been used in various applications, for example, as sanitary materials such as menstrual articles, diapers and disposable napkins or as water retaining agents in agricultural or horticultural uses or for condensation prevention in building materials. As such water absorbing resins, hydrogels using carboxy-methyl cellulose crosslinking products, starch-acrylonitrile graft copolymers, polyvinyl alcohols and polyacrylates as the raw materials have been generally known. However, such hydrogels mentioned above have only one function of starting water absorption upon contact with water.

However, it has been attempted in recent years to further add other functions. For instance, as shown in Japanese Patent Laid-Open Sho 61-55180, a non-ionic hydrogel having a function of reversibly repeating water absorption and discharging, depending on the change of temperature, has been known. That is, the hydrogel scarcely shows water absorption if a water temperature is higher than a certain temperature and can absorb water if the temperature lowers to less than this certain temperature. However, since the hydrogel is non-ionic, it has small water absorbing amount at low temperatures and it is not practical. For increasing the water absorbing amount, a copolymerized hydrogel of n-isopropyl acrylamide and an ionic monomer such as sodium acrylate have been proposed, for example, in U.S. Pat. No. 4,732,930 and J. Chem. Phys. 1987, 87, 1392.

However, although the hydrogel with the ionic monomer described above is improved for water absorbing amount, it involves a drawback that the inherent temperature sensing point (a boundary temperature in which water absorbability exists below the temperature but is almost negligible at a higher temperature) changes greatly by merely copolymerizing the ionic monomer slightly. More specifically, there exits a drawback in that the temperature sensing point rises as the content of the ionic monomer is increased, making it difficult to obtain a composition possessing a temperature sensitivity near room temperature.

Further, various methods have been proposed for improving the water absorbing characteristic of a gel having a sensitive and reversible water absorbing and discharging performance relative to the change of temperature in water. For instance, there have been known, for example, a method of an mixing iron oxide in an aqueous solution of polyvinyl methyl ether under irradiating γ-rays, thereby improving porosity and heat transfer rate resulting in increased water absorbing rate (J. Chem. Eng. Japan, 21, 10, 1988); a method of mixing hydroxyl propyl cellulose to synthesize a gel, cleaning the gel after polymerization to remove hydroxypropyl cellulose, thereby making the gel porous, which improves the water absorbing rate (J. Polym. Soc.: Part A, 30, 2121, 1992); and a method of synthesizing a gel having a nonhomogeneous crosslinking structure by polymerization at a temperature higher than a volume transition temperature (Polymer Communications, 32, 322, 1991). On the other hand, various improvements for increased water absorption have also been conducted on general highly absorbing resins having no water absorbing and discharging performance relative to the change of ambient temperature. For instance, there have been reported, for example, a method of mixing a water absorbing resin powder with hydrotalcite to improve the water absorbing rate (Japanese Patent Laid-Open Hei 2-215863), and a method of mixing a water absorbing resin powder with attapulgite to improve the water absorbing rate (Japanese Patent Laid-Open Sho 61-58657).

However, although conventional methods may improve the water absorbing rate, they involve problems in that the production process for the gel is extremely complicated or the water absorbing rate of the resultant gel is not sufficient.

SUMMARY OF THE INVENTION

A temperature sensitive water absorbing and discharging polymer composition having a predetermined selected temperature sensing point, which controls water absorbability, is obtained by polymerizing in an aqueous solution, N-alkyl acrylamide derivatives with acrylic acid, alkali metal salts of acrylic acid, or mixtures thereof, and diacetone acrylamide. The temperature sensitive water absorbing and water discharging polymer composition is modified to control the temperature sensing point and has a high water discharging and absorbing property above and below the temperature sensing point. The composition is utilized in a wide variety of sanitary materials including sanitary materials such as paper diapers; soil improvers in agricultural and horticultural fields for plants and vegetables such as soil water supplying agents or soil water retaining agents; water proof sealing materials; sandbags; temperature sensors; chemical valves; solid-liquid separation materials; and liquid concentrating materials.

DESCRIPTION OF PREFERRED EMBODIMENTS

The present inventors have made extensive studies for obtaining a resin free from the foregoing drawbacks and, as a result, have found that when N-alkyl acrylamide derivatives and acrylic acid or alkali metal salts of acrylic acid are copolymerized in an aqueous solution, temperature sensitive hydrogels maintaining high water absorbing and discharging properties may be obtained by introducing diacetone acrylamide into the solution. A temperature sensitive point can be adjusted within a wide range at low temperatures by changing the amount of diacetone acrylamide introduced and, therefore, the temperature sensitive point, depending on a desired temperature, may be set easily to complete the present invention.

That is, the present invention provides a temperature sensitive water absorbing and discharging polymer composition obtained by copolymerizing an aqueous solution containing N-isopropyl acrylamide and/or N,N-diethyl acrylamide, acrylic acid and/or alkali metal salts of acrylic acid and diacetone acrylamide in the presence of a crosslinking agent.

The blending amount of the N-isopropyl acrylamide and/or N,N-diethyl acrylamide is desirably from more than 30 mol %, more preferably, more than 50 mol % of the entire monomers used depending on the desired temperature sensitivity, although it also depends on the amount of other monomers used.

Further, as the acrylic acid and/or alkali metal salts of acrylic acid, there can be mentioned, for example, acrylic acid, sodium acrylate, potassium acrylate, calcium acrylate or magnesium acrylate, acrylic acid or sodium acrylate being more preferred. The amount of the acrylic acid and/or alkali metal salt of acrylic acid used, although depending on the kind thereof, is from 0.5 to 40 mol %, more preferably, 1 to 12 mol % based on the total amount of the N-isopropyl acrylamide and/or N,N-diethyl acrylamide, and diacetone acrylamide.

Since diacetone acrylamide is readily soluble in water, it can be used in a wide range of amounts and it is present in amounts from 0.1 to 40 mol % of the entire amount of the monomer used, depending on the desired temperature sensitivity of the resulting material. If diacetone acrylamide is present in amounts less than 0.1 mol %, no substantial effect can be obtained.

Further, as a method of producing a temperature sensitive water absorbing and discharging polymer composition having a crosslinked structure by polymerizing an aqueous monomer solution as described above, a suitable method involves, for example, a method of copolymerizing a divinyl type monomer. Such a method involves copolymerizing a crosslinkable vinyl monomer and then crosslinking the same by a crosslinker or other methods of crosslinking, such as by radioactive rays. The method of copolymerizing the divinyl type monomer is more preferred since the production process is convenient.

As the divinyl type monomer used, a monomer having good copolymerizability with each of the monomers constituting the temperature sensitive polymer, capable of efficiently forming a crosslinked structure, and providing uniform crosslinking distribution, is preferred. Suitable monomers include, for example, N,N-methylenebis(meth) acrylamide, ethylene glycoldi(meth) acrylate, diethylene glycol(meth) acrylate, polyethylene glycoldi(meth)acrylate, propylene glycoldi(meth) acrylate and glycerine tri(meth) acrylate. The amount of the divinyl monomer that may be used ranges from about 0.001 to about 5 wt % and, more preferably, about 0.01 to about 1 wt % based on the weight of the entire monomer.

Further, the inventors of the present application have found that a temperature sensitive water absorbing and discharging composition sensitive to the change of temperature and excellent in water absorbing and discharging rate, is obtained by conducting aqueous solution polymerization in the presence of inorganic particles.

The inorganic particles to be present are optional and one or more materials selected, for example, from acidic white clay, diatomaceous earth and kaolin are preferred.

Referring to the amount of the inorganic particles used, they may be added in amounts ranging from 2 to 50 parts by weight, more preferably, 5 to 20 parts by weight based on 100 parts by weight of the polymer forming ingredients. If they are added in excess of 50 parts by weight, the water absorbing capacity of the resultant temperature sensitive water absorbing and discharging composition is lowered, whereas if the amount of inorganic particles added is less than 2 parts by weight, no noticeable improvement can be obtained for the water absorbing and discharging rate. The inorganic particles have a particle size from 0.001 to 100 µm. If the particle size is greater than 100 µm, dispersibility upon polymerization is inadequate, whereas if the particle size is less than 0.001 µm, no noticeable improvement in water absorbing qualities can be obtained for the water absorbing material.

A process for producing the polymer composition according to the present invention is practiced by dissolving each of monomers forming the temperature sensitive polymer with a divinyl type monomer, added as required, into an aqueous solution, adding to the solution inorganic particles to be present optionally, mixing and dispersing them and then polymerizing the monomer in the presence of a catalyst. Further, if the inorganic fine particles are added and mixed after polymerization or after drying and pulverization of the polymer, uniform dispersion of the organic particles in the material is difficult to achieve or the inorganic particles are not incorporated into the material and, accordingly, no added improvement is possible for the water absorbing rate.

As a process for producing the polymer composition according to the present invention, aqueous solution polymerization is preferable but any other aqueous solution polymerization method may be used. A polymerization initiator used in these methods is a water soluble radical polymerization initiator, for example, hydrogen peroxide or persulfate such as ammonium persulfate or potassium persulfate, hydroperoxides such as t-butyl hydroperoxide or cumene hydroperoxide, or azo type initiators such as 2,2'-azobis(2-amidinopropane) dihydrogen chloride. The water soluble initiator may be combined with, for example, a reducing substance such as sodium hydrogen sulfite or amines such as N,N,N',N'-tetramethylethylene diamine and used as a redox type initiator. The amount of the water soluble radical polymerization initiator used is from 0.01 to 10 wt % and, more preferably, from 0.1 to 2 wt % of the total amount of the composition.

EXAMPLES

The present invention will be explained more specifically with reference to the following examples.

Evaluation for the present invention will be measured by the following methods.

(1) Water Absorbing Rate

After sealing 0.2 g of a temperature sensitive water absorbing and discharging composition of the present invention in a non-woven fabric bag and immersing it in purified water maintained at a temperature of 10° C. for 10 min, the sample is sufficiently drained and weighed. Separately, a non-woven fabric bag not containing the composition is treated in the same manner and it is used as a standard. The weight of the amount of water absorbed by the standard is subtracted from the resultant measured weight, and a value of the bag containing the absorbing and discharging composition calculated per 1 g of the dry composition in the bag is defined as the water absorbing rate. As the value increases, the water absorbing rate also increases.

(2) Water Discharging Rate

After sealing 0.2 g of a temperature sensitive water absorbing and discharging composition of the present invention in a non-woven fabric bag and immersing it in purified water maintained at a temperature of 10° C. for 15 hours, sufficiently causing water to be absorbed, it is placed in purified water maintained at a temperature of 50° C. Water is then drained from the bag for a time until complete draining is achieved (time for reaching a constant weight). This time is defined as a water discharging rate. As the time decreases, the discharging rate increases.

(3) Water Absorbing Amount

After sealing 0.2 g of a temperature sensitive water absorbing and discharging composition of the present invention into a nonwoven fabric bag and immersing it in purified water maintained at a particular temperature for one day, it is sufficiently drained and then weighed. Separately, a nonwoven fabric bag not containing the composition is treated in the same manner and used as a standard. The weight of the standard is subtracted from the obtained measured weight of the bag containing the temperature sensitive water absorbing and discharging composition and a value calculated per 1 g of the dry composition in the bag is defined as a water absorbing amount at each temperature. As the value increase, the water absorbability of the bag increases.

Example 1

In a 500 ml separable flask, 17.82 g of N-isopropyl acrylamide, 1.48 g of an aqueous 40% aqueous solution of sodium acrylate, 8.88 g of diacetone acrylamide, 0.1 g of N,N-methylenebis acrylamide and 150 ml of purified water are added. Then, in a nitrogen atmosphere, 0.24 g of ammonium persulfate and 0.30 ml of N,N,N',N'-tetramethylethylene diamine are added at 10° C. to start polymerization. After the copolymerization is complete, the mixture is warmed and a gel is formed. The gel is removed from the flask and dried in an electric drier at 10° C. The dried gel (resin) is pulverized and the water absorbing amount is measured. The resultant water absorbing amounts at different temperatures are shown in Table 1.

Example 2

The procedure for preparation of the resin in Example 1 is followed except for using 20.03 g of N,N-diethyl acrylamide instead of N-isopropyl acrylamide in Example 1. The water absorbing amounts at different temperatures of the resulting resin are shown in Table 1.

Comparative Example 1

A resin is formed by the same procedure as in Example 1 except that diacetone acrylamide and sodium acrylate are replaced with 23.76 g of N-isopropyl acrylamide in Example 1. The water absorbing amounts at different temperatures of the resulting resin are shown in Table 1.

Comparative Example 2

A resin is formed by the same procedure as in Example 2 except that diacetone acrylamide and sodium acrylate are replaced with 26.71 g of N,N-diethyl acrylamide in Example 2. The water absorbing amounts at different temperatures of the resulting resin are shown in Table 1.

Comparative Example 3

A resin is formed by the same procedure as in Example 1 except that diacetone acrylamide is replaced with 23.76 g of N-isopropyl acrylamide in Example 1. The water absorbing amounts at different temperatures of the resulting resin are shown in Table 1.

Comparative Example 4

A resin is formed by the same procedure as in Example 1 except that diacetone acrylamide is replaced with 4.52 g of methyl acrylate as a hydrophobic monomer in Example 1. The water absorbing amounts at different temperatures of the resulting resin are shown in Table 1.

Comparative Example 5

A resin is formed by the same procedure as in Example 1 except that diacetone acrylamide is replaced with 6.73 g of n-butyl acrylate as a hydrophobic monomer in Example 1. The resulting resin is not dispersed uniformly. Since the resin in this case is not dispersed uniformly, measurements for water absorbing amounts are not conducted.

Comparative Example 6

A resin is formed by the same procedure as in Example 1 except that diacetone acrylamide is replaced with 4.47 g of methacrylamide as a water soluble monomer in Example 1. The water absorbing amount at different temperatures of the resulting resin are shown in Table 1.

Example 3

A resin is formed by the same procedure as in Example 1 except that sodium acrylate is replaced with 1.06 g of acrylic acid, and ammonium sulfate and N,N,N',N'tetramethylethylene diamine are replaced with 0.027 ml of tert-butylhydroperoxide and 0.033 g of LONGARIT (Wako Junyaku) as the polymerization initiator. The water absorbing amounts at different temperatures of the resulting resin are shown in Table 1.

Comparative Example 7

A resin is formed by the same procedure as in Example 1 except that diacetone acrylamide is replaced with 23.76 g of N-isopropyl acrylamide of Example 3. The water absorbing amounts at different temperatures of the resulting resin are shown in Table 1.

Comparative Example 8

A resin is formed by the same procedure as in Example 3 except that diacetone acrylamide is replaced with 4.52 g of methyl acrylate as a hydrophobic monomer 4.52 g of Example 3. The water absorbing amounts at different temperatures of the resulting resin are shown in Table 1.

TABLE 1

| Gel used Water Absorbing Amount | Temperature (°C.) | | | | |
|---|---|---|---|---|---|
| | 10 | 20 | 30 | 40 | 50 |
| Example 1 | 247 | 224 | 57 | 12 | 3 |
| Example 2 | 186 | 128 | 23 | 7 | 3 |
| Comp. Example 1 | 41 | 36 | 25 | 3 | — |
| Comp. Example 2 | 29 | 22 | 5 | 4 | — |
| Comp. Example 3 | 251 | 247 | 240 | 226 | 226 |
| Comp. Example 4 | 266 | 260 | 250 | 199 | 52 |
| Comp. Example 6 | 230 | 226 | 220 | 207 | 193 |
| Example 3 | 142 | 134 | 9 | 2 | — |
| Comp. Example 7 | 150 | 141 | 130 | 15 | 2 |
| Comp. Example 8 | 142 | 125 | 100 | 13 | 3 |

As is apparent from Table 1, the resins according to the present invention maintain higher water absorbability and temperature sensitivity as compared with other resins.

Examples 4–8

Resins of the present invention are formed by the same procedure as in Example 1 except for using the combinations of the amounts of monomers set forth in Table 2. The water absorbing amounts at different temperatures of the resulting resins are shown in Table 3.

TABLE 2

| Example | N-isopropyl acrylamide (g) | Diacetone acrylamide (g) |
|---|---|---|
| 4 | 16.63 | 10.66 |
| 5 | 19.01 | 7.11 |
| 6 | 20.20 | 5.33 |
| 7 | 21.39 | 3.55 |
| 8 | 22.58 | 1.78 |

TABLE 3

| Gel used | Temperature (°C.) | | | | |
|---|---|---|---|---|---|
| | 10 | 20 | 30 | 40 | 50 |
| Water Absorbing Amount | | | | | |
| Example 4 | 200 | 162 | 40 | 9 | 3 |
| Example 5 | 227 | 216 | 141 | 27 | 5 |
| Example 6 | 235 | 224 | 170 | 63 | 12 |
| Example 7 | 228 | 208 | 185 | 96 | 14 |
| Example 8 | 224 | 214 | 194 | 154 | 33 |

Examples 9–12

Resins of the present invention are formed by the same procedure as in Example 3 except for using the combinations of the amounts of monomers set forth in Table and changing the amount of acrylic acid used to 0.47 g. The water absorbing amounts at different temperatures of the resulting resins are shown in Table 5.

TABLE 4

| Example | N-isopropyl acrylamide (g) | Diacetone acrylamide (g) |
|---|---|---|
| 9 | 19.01 | 7.11 |
| 10 | 20.20 | 5.33 |
| 11 | 21.39 | 3.55 |
| 12 | 22.58 | 1.78 |

TABLE 5

| Gel used | Temperature (°C.) | | | | |
|---|---|---|---|---|---|
| | 15 | 20 | 25 | 30 | 35 |
| Water Absorbing Amount | | | | | |
| Example 9 | 68 | 60 | 3 | 2 | 1 |
| Example 10 | 67 | 57 | 24 | 2 | 1 |
| Example 11 | 76 | 72 | 55 | 12 | 2 |
| Example 12 | 85 | 84 | 77 | 62 | 9 |

As is apparent from Tables 3 and 5, the temperature sensitivities of the resins may be changed by changing the amount of diacetone acrylamide introduced while maintaining high water absorbability.

Example 13

300 ml of purified water is charged in a 500 ml separable flask and, under stirring, 20.44 g of N-isopropyl acrylamide, 4.97 g of diacetone acrylamide, 1.06 g of acrylic acidic, 0.14 g of N,N'-methylenebis acrylamide, 2.66 g of acid white clay (N.IKKANITE S-200, manufactured by Nippon Kassei Hakudo Co.) are added, dissolved and dispersed. After cooling under a nitrogen gas stream until the liquid temperature is lowered to 0° C., 0.099 g of LONGARIT and 0.081 ml of t-butyl hydroperoxide are added to conduct polymerization at a constant temperature. After the reaction is completed, a gel is removed from the flask, dried at 10° C. and then pulverized and classified, to obtain a composition (powder) with a grain size of 150 to 500 μm.

Water absorbing rate, water charging rate and water absorbing amount were measured for the resulting composition.

The results are shown in Table 7.

Examples 14–21

Compositions of the present invention are formed by using monomers and inorganic particles as set forth in Table 6 and Table 7, and by the same procedure as in Example 13. The same testing was also conducted on the resulting compositions. The results are shown in Table 6 and Table 7.

(1) Symbols in the tables are defined below.

| Monomer | Inorganic particles |
|---|---|
| NIPAN: N-isopropyl acrylamide | J: Acidic white clay (Nippon Kassei Hakudo) |
| | K: kaolinite (Wako Junyaku) |
| DAAM: Diacetone acrylamide | D: Diatomaceous earth (Wako Junyaku) |
| AAc: Acrylic acid | |
| MBAAm: N,N-methylene-bisacrylamide | |

(2) Unit for the monomer amount (g) Unit for the water absorbing amount at each temperature (g of water absorbed/g of temperature sensitive water absorbing and discharging composition).

TABLE 6

| | EXAMPLES | | | | | |
|---|---|---|---|---|---|---|
| | 13 | 14 | 15 | 16 | 17 | 18 |
| Monomer | AMOUNT | | | | | |
| NIPAN | 20.49 | 20.49 | 20.49 | 20.49 | 20.49 | 20.49 |
| DAAm | 4.97 | 4.97 | 4.97 | 4.97 | 4.97 | 4.97 |
| AAc | 1.06 | 1.06 | 1.06 | 1.06 | 1.06 | 1.06 |
| MBAAm | 0.14 | 0.14 | 0.14 | 0.14 | 0.14 | 0.14 |
| Inorganic particle | | | | | | |
| Kind | J | J | J | J | J | J |
| Amount (g) | 2.66 | 0.27 | 1.33 | 5.32 | 10.64 | 15.96 |
| Water absorbing rate (g/g) | 50 | 12 | 40 | 47 | 45 | 30 |
| Water discharging rate (min) | 40 | 40 | 40 | 40 | 40 | 40 |
| Water absorbing amount at each temperature | | | | | | |
| 10° C. | 120 | 122 | 115 | 122 | 130 | 116 |
| 15° C. | 115 | 118 | 112 | 120 | 125 | 110 |
| 20° C. | 115 | 115 | 110 | 118 | 120 | 105 |
| 25° C. | 110 | 110 | 106 | 115 | 118 | 105 |
| 30° C. | 7 | 6 | 5 | 8 | 6 | 5 |
| 35° C. | 5 | 5 | 5 | 5 | 5 | 5 |
| 40° C. | 5 | 5 | 5 | 5 | 5 | 5 |

TABLE 7

| | EXAMPLES | | |
|---|---|---|---|
| | 19 | 20 | 21 |
| Monomer | Amount | | |
| NIPAN | 20.44 | 20.44 | 20.44 |
| DAAm | 4.97 | 4.97 | 4.97 |
| AAc | 1.06 | 1.06 | 1.06 |
| MBAAm | 0.14 | 0.14 | 0.14 |
| Inorganic particle | | | |
| Kind | K | D | |
| Amount | 2.66 | 2.66 | 0.00 |
| Water absorbing rate (g/g) | 45 | 43 | is |
| Water discharging rate (min) | 40 | 40 | 85 |
| Water absorbing amount at each temperature | | | |
| 10° C. | 118 | 135 | 122 |
| 15° C. | 117 | 132 | 118 |
| 20° C. | 110 | 128 | 108 |

TABLE 7-continued

| | EXAMPLES | | |
|---|---|---|---|
| 25° C. | 60 | 110 | 105 |
| 30° C. | 7 | 10 | 8 |
| 35° C. | 5 | 5 | 3 |
| 40° C. | 5 | 5 | 3 |

As described above, the feature of the present invention resides in introducing diacetone acrylamide as a water soluble monomer for controlling the water absorbing temperature sensitivity of a composition while still maintaining a high water absorbing factor at low temperatures.

A method of introducing a hydrophobic monomer for controlling the temperature sensing point to a low temperature region has been known. However, since the hydrophobic monomer has a low water solubility, it involves drawbacks, for example, in that polymerization in an aqueous solution is impossible or, even if possible, optional control of the temperature sensitivity of the resulting composition is impossible since the amount of monomer introduced into the composition is limited. Further, the concentration of the monomer upon polymerization must be reduced to an extremely low concentration. For instance, methyl acrylate, known as a hydrophobic monomer, has a water solubility of about 6%, and an inhomogeneous polymerizate is formed at concentrations higher than 6%. Further, assuming the water absorbing amount at 10° C. is 100 and the temperature at which the water absorbing amount is reduced to 50 is defined as the temperature sensing point, the temperature sensing point of the polymer is lowered only by 1.7° C. in a case of introducing 10 mol % of methyl acrylate as described in Comparative Example 8, whereas the temperature sensing point is lowered as much as by 7° C. when using diacetone acrylamide as described in Examples 9–12. Since diacetone acrylamide used in the present invention is a water soluble monomer and dissolves in water at a variable ratio, a homogeneous resin can be produced easily and the content can be varied optionally. Accordingly, the present invention has the advantage of easily setting the temperature sensitivity of a water absorbing and discharging composition while maintaining a high water absorbing amount.

As has been explained above, since the temperature sensitive water absorbing and discharging composition according to the present invention may control the temperature sensitivity with high water discharging and absorbing properties above and below a temperature sensing point, it can be utilized in a wide variety of applications. For example, the composition of the present invention may be utilized in sanitary materials such as paper diapers, soil improvers in agricultural and horticultural fields for plants and vegetables such as soil water feeding agents or soil water retaining agents, water proof sealing materials, sandbags, temperature sensors, chemical valves, solid-liquid separation aids and liquid concentrating materials.

What is claimed is:

1. A temperature sensitive water absorbing and discharging polymer composition, comprising in an aqueous solution, a copolymer of N-alkyl acrylamide derivatives with acrylic acid, alkali metal salts of acrylic acid or mixtures thereof, said composition further comprising diacetone acrylamide, wherein said N-alkyl acrylamide derivatives are N-isopropyl acrylamide, N-N-diethyl acrylamide, or mixtures thereof.

2. A composition according to claim 1, wherein said alkali metal salts of acrylic acid are sodium acrylate, potassium acrylate, or mixtures thereof.

3. A composition according to claim 1, wherein said composition further comprises a crosslinking agent.

4. A composition according to claim 3, wherein said crosslinking agent is a divinyl monomer.

5. A composition according to claim 1, wherein said composition further comprises inorganic particles.

6. A composition according to claim 5, wherein said inorganic particles are selected from the group consisting of acidic white clay, diatomaceous earth, kaolinite and mixtures thereof.

7. A composition according to claim 5, wherein said inorganic particles are present in said composition in an amount of 2–50 parts by weight based on 100 parts by weight of said composition.

8. A composition according to claim 5, wherein said inorganic particles have a particle size from 0.001 to 100 μm.

9. A composition according to claim 1, wherein said N-alkyl acrylamide derivative is present in an amount of more than 30 mol % based on the total amount of monomers present in the composition.

10. A composition according to claim 1, wherein said acrylic acid, said alkali metal salts of acrylic acid or mixtures thereof is present in an amount of 0.5 to 40 mol % based on the total amount of monomers present in the composition.

11. A composition according to claim 1, wherein said diacetone acrylamide is present in an amount of 0.1 to 40 mol % based on the total amount of the monomers present in the composition.

12. A composition according to claim 4, wherein said divinyl monomer is selected from the group consisting of N,N-metheylenebis(meth)acrylamide, ethylene glycoldi(meth) acrylate, diethylene glycol(meth) acrylate, polyethylene glycoldi(meth)acrylate, propylene glycoldi(meth) acrylate, glycerine tri(meth) acrylate and mixtures thereof.

13. A composition according to claim 4, wherein said divinyl monomer is present in an amount of about 0.001 to about 5 wt. % based on the total amount of monomers present in said composition.

14. A product made from the composition of claim 1 comprising sanitary materials, soil water feeding agents, soil water retaining agents, waterproof sealing materials, sandbags, temperature sensors, chemical valves, solid-liquid separation materials and concentrating materials.

15. A method for producing a temperature sensitive water absorbing and discharging polymer composition, comprising copolymerizing in an aqueous solution at least one N-alkyl acrylamide derivative with at least one member selected form the group consisting of acrylic acid, alkali metal salts of acrylic acid and mixtures thereof, said solution further comprising diacetone acrylamide, wherein said N-alkyl acrylamide derivatives are N-isopropyl acrylamide, N-N-diethyl acrylamide, or mixtures thereof.

16. A method according to claim 15, wherein the said alkyl metal salts of acrylic acid are sodium acrylate, potassium acrylate, calcium acrylate, magnesium acrylate or mixtures thereof.

17. A method according to claim 15, wherein the said solution further comprises a crosslinking agent.

18. A method according to claim 15, wherein the said solution further comprises a polymerization initiator.

19. A method according to claim 15, wherein the said solution further comprises inorganic particles.

20. A temperature sensitive water absorbing and discharging polymer composition made by the method of claim 15.

* * * * *